(12) United States Patent
Blomberg et al.

(10) Patent No.: US 6,242,174 B1
(45) Date of Patent: Jun. 5, 2001

(54) DISCRIMINATION BETWEEN ANTIBODIES AGAINST HTLV-I, HTLV-II OR RELATED RETROVIRUSES, NEW PEPTIDES, DETECTION OF ANTIBODIES AND IMMUNOASSAY KITS

(75) Inventors: Jonas Blomberg, Lomma (SE); Rüdiger Pipkorn, Heidelberg (DE)

(73) Assignee: Replico Medical AB, Lomma (SE)

( * ) Notice: Subject to any disclaimer, the term of this patent is extended or adjusted under 35 U.S.C. 154(b) by 0 days.

(21) Appl. No.: 07/752,639

(22) Filed: Oct. 7, 1991

(30) Foreign Application Priority Data

Mar. 2, 1989 (SE) .................................................... 8900721
Mar. 2, 1990 (WO) .................................. PCT/SE90/00139

(51) Int. Cl.$^7$ .................................................... C12Q 1/70
(52) U.S. Cl. ................................ 435/5; 435/7.1; 435/974; 435/975; 530/324; 530/325; 530/326; 530/328; 530/826; 530/327
(58) Field of Search ................................ 435/5, 7.1, 974, 435/975; 530/300, 324–328, 826

(56) References Cited

U.S. PATENT DOCUMENTS

| | | | |
|---|---|---|---|
| 4,525,300 | 6/1985 | Yoshida et al. | 260/112.5 |
| 4,689,398 | * 8/1987 | Wu et al. | 435/5 |
| 4,804,746 | 2/1989 | Yoshida et al. | 530/387 |
| 4,833,071 | 5/1989 | Wang et al. | |

FOREIGN PATENT DOCUMENTS

| | | |
|---|---|---|
| 267622 | * 5/1988 | (EP) . |
| 0267622 | 5/1988 | (EP) . |
| 59128366 | 7/1984 | (JP) . |
| 59155347 | 9/1984 | (JP) . |
| WO8601834 | 3/1986 | (WO) . |
| WO8901527 | 2/1989 | (WO) . |
| 8901527 | * 2/1989 | (WO) . |
| WO8908664 | 9/1989 | (WO) . |

OTHER PUBLICATIONS

Cianciolo, Bogerd & Snyderman, Human retrovirus–related synthetic peptides inhibit T lymphocyte proliferation, 19 Immunology Letters pp. 7–14 (1988).

Cianciolo, Copeland, Oroszlan, Snyderman, Inhibition of Lymphocyte Proliferation by a Synthetic Peptide Homologous to Retroviral Envelope Proteins, Science, vol. 230,No. 4724,pp. 453–455,Oct. 25, 1985.

Asher DM, Goudsmit J., Pomeroy KL, Garruto RM, Bakker M, Ono SG, Elliott N, Harris K., Askins H., Eldadah Z., Goldstein AD, Gajdusek DC. Antibodies to HTLV–I in populations of the southwestern Pacific. J. Med. Virol 26:339–351 (1988).

Ben–Ishai Z., Haas M., Triglia D., Lee V., Nahmias J., Bar–Shany S, Jensen F. Human T–cell lymphotropic virus type I antibodies in Falashas and other ethnic groups in Israel. Nature 315:665–666 (1985).

Blattner WA, Nomura A., Clark JW, Ho GYF, Nakao Y., Gallo R., Robert–Guroff M. Modes of transmission and evidence for viral latency from studies of human T–cell lymphotropic virus type I in Japanese migrant populations in Hawaii. Proc Natl Acad Sci USA 83:4895–4898 (1986).

Blomberg J., Nilsson I., Andersson M. Viral antibody screening system that uses a standardized single dilution immunoglobulin G enzyme immunoassay with multiple antigens. J Clin Microbiol 17:1081–1091 (1983).

Blomberg J., Nilsson I., Kjellen L. HTLV in Sweden: Antibodies to HTLV I antigens in experimental monkeys and their caretakers. Scand J. Infect Dis 17:135–139 (1985).

Blomberg J. HTLV–I –prototyp i en vaxande grupp av leukemogena virus. Lakartidningen 86:2294–2295 (1989).

Bruck C., Portetelle D., Burny A., Zavada J. Topographical analysis by monoclonal antibodies of BLV–gp51 epitopes involved in viral functions. Virology 122:353–362 (1982).

Cogniaux J., Jacquemain PC. Production of monoclonal antibodies against HTLV–I proteins recognizing surface epitopes of live infected cells. Leukemia Research 9:1117–1126 (1985).

Clapham P., Nagy K., Weiss RA. Pseudotypes of human T–cell leukemia virus types 1 and 2: Neutralization by patients' sera. Proc Natl Acad Sci USA 81:3083–3086 (1984).

Chen I.S.Y., McLaughlin J., Gasson JC, Clark SC, Golde DW. Molecular characterization of genome of a novel human T–cell leukemia virus. Nature 305: 502–505 (1983).

De Rossi A., Bortolotti F., Cadrobbi P., Chieco–Bianchi L. Trends of HTIV–I and HIV infections in drug addicts. Eur J Cancer Clin Oncol 24:279–280 (1988).

Dracopoli NC, Turner TR, Else JG, Jolly CJ, Anthony R., Gallo RC, Saxinger WC. STLV–I antibodies in feral populations of East African vervet monkeys (*Cercopithecus aethiops*). Int J Cancer 38: 523–529 (1986).

(List continued on next page.)

*Primary Examiner*—Jeffery Stucker
(74) *Attorney, Agent, or Firm*—Pitney, Hardin, Kipp & Szuch, LLP

(57) ABSTRACT

A method of discriminating between specific antibodies in samples of sera or other body fluids from humans or other primates containing antibodies arising from infection with HTLV-I, containing antibodies arising from infection with HTLV-II or containing antibodies arising from infection with related retroviruses, is described. In said method, the sample to be analyzed is subjected to at least four immunoassays, each using a different diagnostic antigen selected from four defined groups of peptides.

Figure 1:
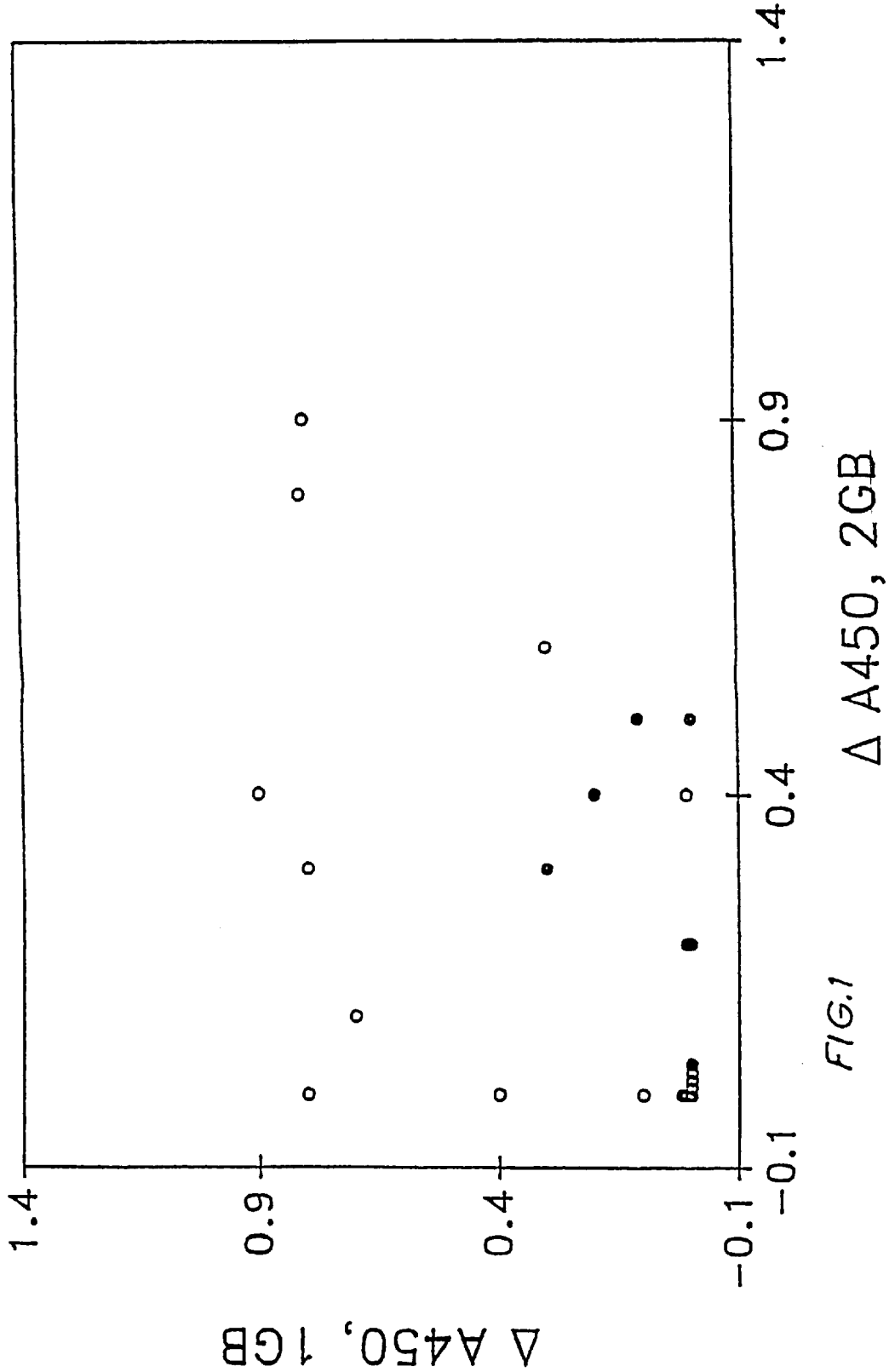

Additionally, an immunoassay kit adapted for said method of discrimination, new peptides and a method of detecting antibodies with said peptides, are described.

10 Claims, 3 Drawing Sheets

OTHER PUBLICATIONS

Gallo RC, Kalyanaraman VS, Sarngadharan MG, Sliski A., Vonderheid EC, Maeda M., Nakao Y., Yamada K., Ito Y., Gutensohn N., Murphy S., Bunn Jr., PA, Catovsky D., Greaves MF, Blayney DW, Blattner WA, Jarrett WFH, Zur Hausen H., Seligmann M., Brouet JC, Haynes BF, Jegasothy BV, Jaffe ES, Cossman J., Broder S., Fisher RI, Golde DW, Robert–Guroff M. Association of the human type–C retrovirus with a subset of adult T–cell cancers. Cancer Res 43:3892–3899 (1983).

Jason JM, McDougal S., Cabradilla C., Kalyanaraman VS, Evatt BL. Human T–cell leukemia virus (HTLV–I) p24 antibody in New York city blood product recipients. Amer J Hematol 20:129–137 (1985).

Klasse PJ, Pipkorn R., Blomberg J. Presence of anti–bodies to a putatively immunosuppressive part of human immunodeficiency virus (HIV) envelope glycoprotein gp41 is strongly associated with health among HIV–positive subjects. Proc Natl Acad Sci USA 85:5225–5229 (1988).

Kalyanaraman VS, Sarngadharan MG, Poiesz B., Ruscetti FW, Gallo RC. Immunological properties of a type C retrovirus isolated from cultured human T–lymphoma cells and comparison to other mammalian retroviruses. J Virol 38:906–915 (1981).

Lee H., Swanson P., Shorty VS, Zack JA, Rosenblatt JD, Chen IS. High rate of HTLV–II infection in seropositive i.v. drug abusers in New Orleans. Science 28:471–475 (1989).

Lee TH, Coligan JE, McLane MF, Sodroski JG, Popovic M., Wong–Staal F., Gallo RC, Haseltine W., Essex M. Serological cross–reactivity between envelope gene products of type I and type II human T–cell leukemia virus. Proc Natl Acad Sci USA 81:7579–7583 (1984).

Manzari V., Gradilone A, Barillari G., Zani M., Collalti E., Pandolfi F., De Rossi G., Liso V., Babbo P., Robert–Guroff M., Frati L. HTLV–I is endemic in southern Italy: Detection of the first infectious cluster in a white population. Int J Cancer 36:557–559 (1985).

Osame M., Matsumoto M., Usuku K., Izumo S., Ijichi N., Amitani H., Tara M., Igata A. Chronic progressive myelopathy associated with elevated antibodies to human T–lymphotropic virus type I and adult T–cell leukemialike cells. Ann Neurol 21:117–122 (1987).

Robert–Guroff M., Gallo RC. Establishment of an etiologic relationship between the human T–cell leukemia/lymphoma virus (HTLV) and adult T–cell leukemia. Blut 47:1–12 (1983).

Tanaka Y., Lee B., Inoi T., Tozawa H., Yamamoto N., Hinuma Y. Antigens related to three core proteins of HTLV–I (p24, p19 and p15) and their intracellular localizations, as defined by monoclonal antibodies, Int J Cancer 37:35–42 (1986).

Tedder RS, Shanson DC, Jeffries DJ, Cheingsong–Popov R., Clapham P., Dalgleish A., Nagy K., Weiss RA. Low prevalence in the UK of HTLV–I and HTLV–II infection in subjects with AIDS, with extended lymphadenopathy, and at risk of AIDS. Lancet ii: 125–128 (1984).

Tozawa H., Andoh S., Takayama Y., Tanaka Y., Lee B., Nakamura H., Hayami M., Hinuma Y. Species–dependent anti–genicity of the 34–kDa glycoprotein found on the membrane of various primate lymphocytes transformed by human T–cell leukemia virus type I (HTLV–I) and simian T–cell leukemia virus (STLV–I). Int. J Cancer 41:231–238 (1988).

Weiss RA, Clapham P., Nagy K., Hoshino H. Envelope properties of human T–cell leukemia viruses. Curr Top Microbiol Immunol 115: 235–246 (1985).

White PM. Comparison of assays for antibody to HTLV–I. J Clin Pathol 41:700–702 (1988).

Williams AE, Fang TC, Slamon DJ, Poiesz BJ, Sandler GS, Darr II F., Shulman G., McGowan EI, Douglas DK, Bowman RJ, Peetom F., Kleinman SH, Lenes B., Dodd RY. Seroprevalence and epidemiological correlates of HTLV–I infection in US blood donors. Science 240:643–646 (1988).

"Nucleotide Sequence Analysis of Human T–cell Leukemia Virus Type II" by Shimotohno, Takahashi, Shimizu, Takano, Miwa and Sugimura from "Retroviruses in Human Lymphoma/Leukemia" M. Miwa et al (EDS.); Japan Sci. Soc. Press, Tokyo/VNU Science Press, Utrecht, pp 165–175, 1985.

"Human T–Cell Leukemia Virus Type II; Primary Structure Analysis of the Major Internal Protein, p24 and the Nucleic Acid Binding Protein, p15" by Devare, Kim, Fox Getchell, Cabradilla and Kalyanaraman from "Virology 142" pp. 206–210 (1985).

Seiki et al, PNAS (80) 1983. pp 3618–3622.*

Kalyanaraman et al, Science 218, 1982, p 571–573.*

Robert–Gerroff et al, JAMA 255(22) 1986, pp 3133–3137.*

Palker et al, J. of Immunol. 136(7) 1986. pp 2393–2397.*

Amit et al, Science 233, 1986. pp747–753.*

Shimotohno et al, PNAS 82, 1985. pp 3101–3105.*

Sodrowski et al, Science 225, 1984. pp 421–424.*

Kalyanaramen et al, Virology 132, 1984. pp 61–70.*

Norsby et al, Natue 329, 1987. pp 248–250.*

Palker et al, J. Immunol 142(1089) p971–978.*

Thomas J. Palker, Mary E. Tanner, Richard M. Scearce, et al. The Journal of Immunology, vol. 142.971–978, No. 3 Feb. 1, 1989.

Thomas J. Palker, Richard M. Scearce, Winifred Ho, et al. The Journal of Immunology, vol. 135, No. 1, Jul. 1985 pp. 247–254.

Erling Norrby, Gunnel Biberfeld, Francesca Chiodi, et al. Nature, vol. 329, Sep. 17, 1987 pp. 248–250.

* cited by examiner

DISCRIMINATION BETWEEN ANTIBODIES AGAINST HTLV-I, HTLV-II OR RELATED RETROVIRUSES, NEW PEPTIDES, DETECTION OF ANTIBODIES AND IMMUNOASSAY KITS

The present invention relates to a method of discriminating between specific antibodies in samples of sera or other body fluids from humans or other primates containing antibodies arising from infection with HTLV-I, HTLV-II or related retroviruses. Additionally, it relates to an immunoassay kit adapted for said method of discrimination, and new peptides and a method of detecting antibodies with said peptides.

BACKGROUND

Up to now the following techniques for differentiating infection with the two viruses have been used: Virus isolation with typing, serological techniques (based on antibody competition or neutralization), or nucleic acid techniques (nucleic acid amplification or hybridization). Most of these techniques are laborious and require special competence.

Human T-lymphotropic virus type I (HTLV-I) and type II (HTLV-II) are widespread human retroviruses (a short review is given in ref. 6) (1, 2, 3, 20). HTLV-II has for several years been considered to be rare, but has recently proved to be a rather common infection among intravenous drug abusers primarily in the United States of America. The viruses cross-react serologically. It is therefore impossible to discriminate between an infection with one virus from an infection with the other with current antibody tests. It may prove clinically important to differentiate between infections with the two viruses. HTLV-I is associated with a type of leukemia (Adult T cell Leukemia; ATL) while HTLV-II has been observed in a few cases of hairy cell leukemia. There is a need for simple tests to differentiate between the two infections.

Even if the amino acid sequences of HTLV-I and HTLV-II proteins are similar there are several regions where they are markedly different. Our idea is to use synthetic peptides from such regions as antigens in antibody tests. We have found peptides with sequences which e.g. are suitable for solid phase immunoassays and which give a type-specific antibody reactivity. We have found techniques where we use them to discern infection with HTLV-I from infection with HTLV-II.

DESCRIPTION OF THE INVENTION

One aspect of the invention is directed to a method of discriminating between specific antibodies in samples of sera or other body fluids from humans or other primates containing antibodies arising from infection with HTLV-I, containing antibodies arising from infection with HTLV-II or containing antibodies arising from infection with related retroviruses, whereby the sample to be analyzed is subjected to at least four immunoassays, each using a different diagnostic antigen selected from the following groups a) to d):

a) peptides comprising a sequence of at least 17 amino acid residues which corresponds to a sequence of HTLV-I gag comprising antigenic structures;

b) peptides comprising a sequence of at least 17 amino acid residues which corresponds to a sequence of HTLV-II gag comprising antigenic structures;

c) peptides comprising a sequence of at least 17 amino acid residues which corresponds to a sequence of HTLV-I env comprising antigenic structures;

d) peptides comprising a sequence of at least 17 amino acid residues which corresponds to a sequence of HTLV-II env comprising antigenic structures;

with the proviso that at least one peptide from each of the groups a) to d) is selected and, further, that at least one pair of peptides corresponding to at least partially overlapping sequences of HTLV-I and HTLV-II is selected from each of the groupages a) plus b), and c) plus d), and that the analyzed, different binding strengths of the antibodies of the sample in said at least four immunoassays are used to discriminate between antibodies arising from infection with one specific retrovirus and antibodies arising from infection with other specific retroviruses.

In an embodiment of this aspect of the invention the diagnostic antigens are selected in the above manner from the peptides:

| | | |
|---|---|---|
| a) HTLV-I | gag 130–197 | PVMHPHGAPPNHRPWQMKDLQAIKQE-VSQAAPGSPQFMQTIRLAVQQFDPTA-KDLQDLLQYLCSSLVA |
| b) HTLV-I | gag 137–214 | PILHPPGAPSAHRPWQMKDLQAIKQEV-SSSALGSPQFMQTLRLAVQQFDPTAKD-LQDLLQYLCSSLVV |
| a) HTLV-I | gag 298–349 | LRSLAYSNANKECQKLLQARGHTNSPL-GDMLRACQTWTPKDKTKVLVVQPKK |
| b) HTLV-II | gag 305–356 | LRSLAYSNANKECQKILQARGHTNSPL-GEMLRTCQAWTPKDKTKVLVVQPRR |
| a) HTLV-I | gag 4–20 | IFSRSASPIPRPPRGLA |
| b) HTLV-II | gag 4–20 | IHGLSPTPIPKAPRGLS |
| a) HTLV-I | gag 111–130 | PDSDPQIPPPYVEPTAPQVL |
| b) HTLV-II | gag 117–136 | PSPEAHVPPPYVEPTTTQCP |
| a) HTLV-I | gag 265–285 | SILQGLEEPYHAFVERLNIAL |
| a) HTLV-I | gag 302–320 | LAYSNANKECQKLLQARGH |
| a) HTLV-I | gag 323–341 | SPLGDMLRACQTWTPKDKT |
| a) HTLV-I | gag 337–355 | PKDKTKVLVVQPKKPPPNQ |
| b) HTLV-II | gag 343–361 | PKDKTKVLVVQPRRPPPTQ |
| a) HTLV-I | gag 378–399 | PCPLCQDPTHWKRDCPRLKPT |
| a) HTLV-I | gag 392–411 | DCPRLKPTIPEPEPEEDALL |
| b) HTLV-II | gag 398–416 | DCPQLKPPQEEGEPLLLDL |
| c) HTLV-I | env 190–213 | LLPHSNLDHILEPSIPWKSKLLTL |
| d) HTLV-II | env 186–209 | LVHDSDLEHVLTPSTSWTTKILKF |
| c) HTLV-I | env 290–312 | HNSLILPPFSLSPVPTLGSRSRR |
| c) HTLV-I | env 360–378 | AIVKNHKNLLKIAQYAAQN |
| c) HTLV-I | env 376–392 | AQNRRGLDLLFWEQGGL |
| c) HTLV-I | env 380–398 | RGLDLLFWEQGGLCKALQE |
| c) HTLV-I | env 465–488 | RQLRHLPSRVRYPHYSLILPESSL |
| d) HTLV-II | env 463–486 | IQALPQRLQNRHNQYSLINPETML |

In a preferred embodiment at least the following peptides are selected:

| | | |
|---|---|---|
| a) HTLV-I | gag 111–130 | PDSDPQIPPPYVEPTAPQVL |
| b) HTLV-II | gag 117–136 | PSPEAHVPPPYVEPTTTQCP |
| c) HTLV-I | env 190–213 | LLPHSNLDHILEPSIPWKSKLLTL |
| d) HTLV-II | env 185–209 | LVHDSDLEHVLTPSTSWTTKILKF |

In a further preferred embodiment the sample to be analyzed is subjected to at least eight immunoassays and the analyzed pattern of binding strengths is processed with a computer program.

Optionally, at least one of the selected peptides is attached to an inert soluble or insoluble carrier.

Another aspect of the invention is directed to a peptide, which corresponds to a sequence of HTLV-I, HTLV-II or a related retrovirus each comprising antigenic structures and which comprises a sequence of at least 17 amino acid residues selected from the following sequences:

| | | |
|---|---|---|
| HTLV-I | gag 130–197 | PVMHPHGAPPNHRPWQMKDLQAIKQE-VSQAAPGSPQFMQTIRLAVQQFDPTA-KDLQDLLQYLCSSLVA |

-continued

| | | |
|---|---|---|
| HTLV-I | gag 137–214 | PILHPPGAPSAHRPWQMKDLQAIKQEV-SSSALGSPQFMQTLRLAVQQFDPTAKD-LQDLLQYLCSSLVV |
| HTLV-I | gag 298–349 | LRSLAYSNANKECQKLLQARGHTNSPL-GDMLRACQTWTPKDKTKVLVVQPKK |
| HTLV-II | gag 305–356 | LRSLAYSNANKECQKILQARGHTNSPL-GEMLRTCQTWAPKDKTKVLVVQPRR |
| HTLV-I | gag 4–20 | IFSRSASPIPRPPRGLA |
| HTLV-II | gag 4–20 | IHGLSPTPIPKAPRGLS |
| HTLV-I | gag 111–130 | PDSDPQIPPPYVEPTAPQVL |
| HTLV-II | gag 117–136 | PSPEAHVPPPYVEPTTTQCP |
| HTLV-I | gag 265–285 | SILQGLEEPYHAFVERLNIAL |
| HTLV-I | gag 302–320 | LAYSNANKECQKLLQARGH |
| HTLV-I | gag 323–341 | SPLGDMLRACQTWTPKDKT |
| HTLV-I | gag 337–355 | PKDKTKVLVVQPKKPPPNQ |
| HTLV-II | gag 343–361 | PKDKTKVLVVQPRRPPPTQ |
| HTLV-I | gag 378–399 | PCPLCQDPTHWKRDCPRLKPT |
| HTLV-I | gag 392–411 | DCPRLKPTIPEPEPEEDALL |
| HTLV-II | gag 398–416 | DCPQLKPPQEEGEPLLLDL |
| HTLV-I | env 190–213 | LLPHSNLDHILEPSIPWKSKLLTL |
| HTLV-II | env 186–209 | LVHDSDLEHVLTPSTSWTTKILKF |
| HTLV-I | env 290–312 | HNSLILPPFSLSPVPTLGSRSRR |
| HTLV-I | env 360–378 | AIVKNHKNLLKIAQYAAQN |
| HTLV-I | env 376–392 | AQNRRGLDLLFWEQGGL |
| HTLV-I | env 380–398 | RGLDLLFWEQGGLCKALQE |
| HTLV-I | env 465–488 | RQLRHLPSRVRYPHYSLILPESSL |
| HTLV-II | env 463–486 | IQALPQRLQNRHNQYSLINPETML |

Yet another aspect of the invention is directed to a method of detecting antibodies arising from infection with HTLV-I, HTLV-II or a related retrovirus in a sample of serum or other body fluid from a human or an other primate, whereby said sample is subjected to an immunoassay using as a diagnostic antigen at least one peptide of the invention.

Still another aspect of the invention is directed to an immunoassay kit for the discrimination between samples of sera or other body fluids from humans or other primates containing antibodies arising from infection with HTLV-I, containing antibodies arising from infection with HTLV-II or containing antibodies arising from infection with related retroviruses, which kit comprises at least four peptides selected from the following groups a) to d):

a) peptides comprising a sequence of at least 17 amino acid residues which corresponds to a sequence of HTLV-I gag comprising antigenic structures;

b) peptides comprising a sequence of at least 17 amino acid residues which corresponds to a sequence of HTLV-II gag comprising antigenic structures;

c) peptides comprising a sequence of at least 17 amino acid residues which corresponds to a sequence of HTLV-I env comprising antigenic structures;

d) peptides comprising a sequence of at least 17 amino acid residues which corresponds to a sequence of HTLV-II env comprising antigenic structures;

with the proviso that it comprises at least one peptide from each of the groups a) to d) and, further, that it comprises at least one pair of peptides corresponding to at least partially overlapping sequences of HTLV-I and HTLV-II from each of the groupages a) plus b), and c) plus d).

In an embodiment of this aspect of the invention the immunoassay kit comprises at least four peptides selected in the above manner from the peptides:

| | | |
|---|---|---|
| a) HTLV-I | gag 130–197 | PVMHPHGAPPNHRPWQMKDLQAIKQE-VSQAAPGSPQFMQTIRLAVQQFDPTA-KDLQDLLQYLCSSLVA |

-continued

| | | |
|---|---|---|
| b) HTLV-I | gag 137–214 | PILHPPGAPSAHRPWQMKDLQAIKQEV-SSSALGSPQFMQTLRLAVQQFDPTAKD-LQDLLQYLCSSLVV |
| a) HTLV-I | gag 298–349 | LRSLAYSNANKECQKLLQARGHTNSPL-GDMLRACQTWTPKDKTKVLVVQPKK |
| b) HTLV-II | gag 305–356 | LRSLAYSNANKECQKILQARGHTNSPL-GEMLRTCQAWTPKDKTKVLVVQPRR |
| a) HTLV-I | gag 4–20 | IFSRSASPIPRPPRGLA |
| b) HTLV-II | gag 4–20 | IHGLSPTPIPKAPRGLS |
| a) HTLV-I | gag 111–130 | PDSDPQIPPPYVEPTAPQVL |
| b) HTLV-II | gag 117–136 | PSPEAHVPPPYVEPTTTQCP |
| a) HTLV-I | gag 265–285 | SILQGLEEPYHAFVERLNIAL |
| a) HTLV-I | gag 302–320 | LAYSNANKECQKLLQARGH |
| a) HTLV-I | gag 323–341 | SPLGDMLRACQTWTPKDKT |
| a) HTLV-I | gag 337–355 | PKDKTKVLVVQPKKPPPNQ |
| b) HTLV-II | gag 343–361 | PKDKTKVLVVQPRRPPPTQ |
| a) HTLV-I | gag 378–399 | PCPLCQDPTHWKRDCPRLKPT |
| a) HTLV-I | gag 392–411 | DCPRLKPTIPEPEPEEDALL |
| b) HTLV-II | gag 398–416 | DCPQLKPPQEEGEPLLLDL |
| c) HTLV-I | env 190–213 | LLPHSNLDHILEPSIPWKSKLLTL |
| d) HTLV-II | env 186–209 | LVHDSDLEHVLTPSTSWTTKILKF |
| c) HTLV-I | env 290–312 | HNSLILPPFSLSPVPTLGSRSRR |
| c) HTLV-I | env 360–378 | AIVKNHKNLLKIAQYAAQN |
| c) HTLV-I | env 376–392 | AQNRRGLDLLFWEQGGL |
| c) HTLV-I | env 380–398 | RGLDLLFWEQGGLCKALQE |
| c) HTLV-I | env 465–488 | RQLRHLPSRVRYPHYSLILPESSL |
| d) HTLV-II | env 463–486 | IQALPQRLQNRHNQYSLINPETML |

In a preferred embodiment of this aspect of the invention the immunoassay kit comprises at least the following peptides:

| | | |
|---|---|---|
| a) HTLV-I | gag 111–130 | PDSDPQIPPPYVEPTAPQVL |
| b) HTLV-II | gag 117–136 | PSPEAHVPPPYVEPTTTQCP |
| c) HTLV-I | env 190–213 | LLPHSNLDHILEPSIPWKSKLLTL |
| d) HTLV-II | env 185–209 | LVHDSDLEHVLTPSTSWTTKILKF |

SHORT DESCRIPTION OF THE DRAWINGS

FIG. 1. Distribution of antibody reactivity with the peptide pair 1GB/2GB. Data from 15 HTLV-I and 10 HTLV-II positive sera from USA. Filled circles=HTLV-II positive sera.

Figure 2:
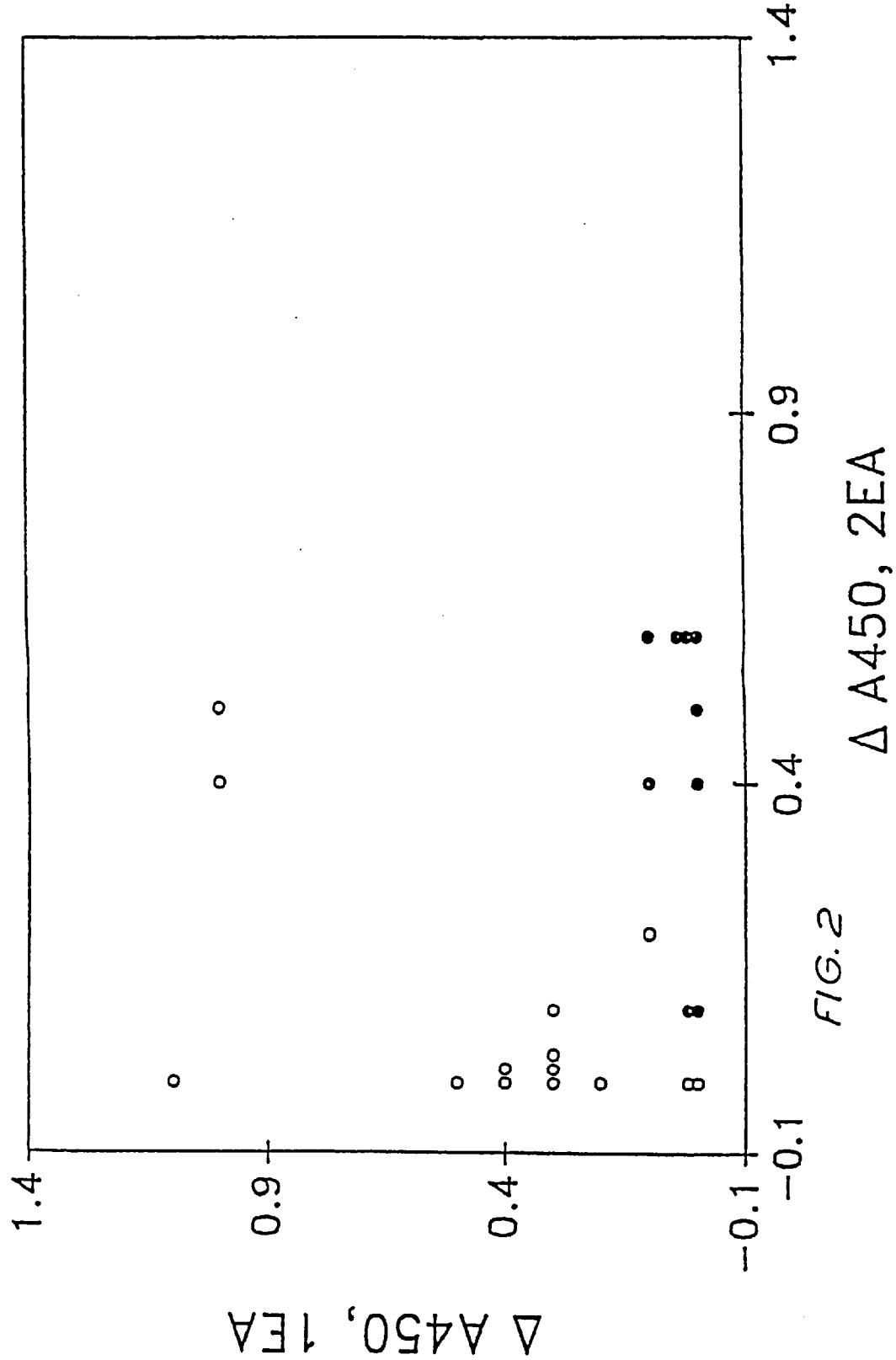

FIG. 2. Distribution of antibody reactivity with the peptide pair 1EA/2EA. Symbols and sera as in FIG. 1.

Figure 3:
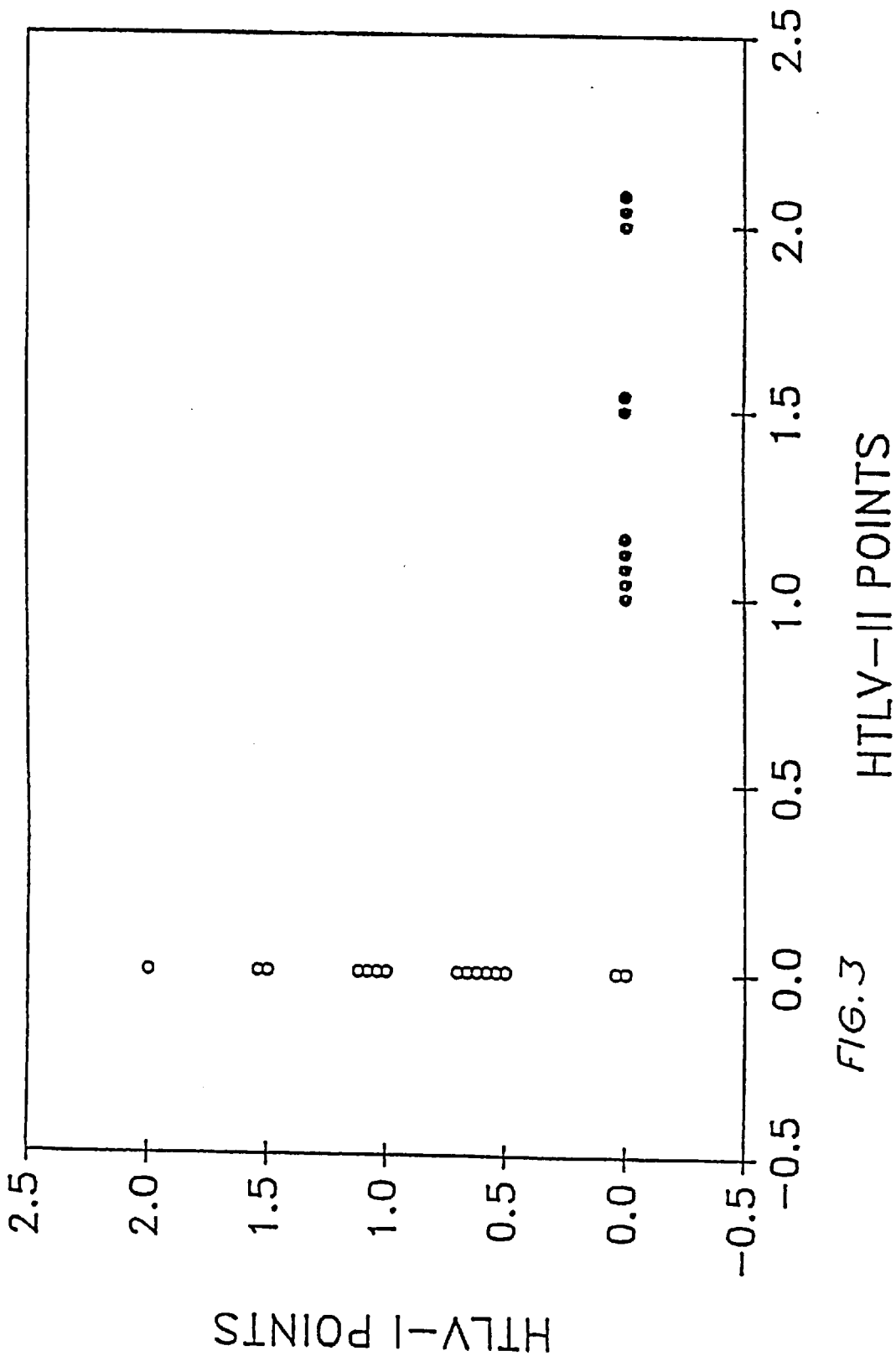

FIG. 3. Classification of serological reactivity with the help of the computer program HTLVPARS. HTLV-I and HTLV-II points have been computed with the same sera as in FIGS. 1 and 2, and are shown with the same symbols. One-Letter Code for Amino Acids.

In the specification and claims the following conventional one-letter code is used:

A Alanine
C Cysteine
D Aspartic acid
E Glutamic acid
F Phenylalanine
G Glycine
H Histidine
I Isoleucine
K Lysine
L Leucine
M Methionine
N Asparagine
P Proline
Q Glutamine
R Arginine
S Serine
T Threonine
V Valine
W Tryptophan
Y Tyrosine

MATERIAL

Synthetic Peptides

The following peptides were synthesized. The letters to the left in the following symbolize the peptides employed.

| | | |
|---|---|---|
| 1GA HTLV-I | gag 4–20 | IFSRSASPIPRPPRGLA |
| 2GA HTLV-II | gag 4–20 | IHGLSPTPIPKAPRGLS |
| 1GB HTLV-I | gag 111–130 | PDSDPQIPPPYVEPTAPQVL |
| 2GB HTLV-II | gag 117–136 | PSEAHVPPPYVEPTTTQCP |
| 1GC HTLV-I | gag 265–285 | SILQGLEEPYHAFVERLNIAL |
| 1GD HTLV-I | gag 302–320 | LAYSNANKECQKLLQARGH |
| 1GE HTLV-I | gag 323–341 | SPLGDMLRACQTWTPKDKT |
| 2GF HTLV-I | gag 337–355 | PKDKTKVLVVQPKKPPPNQ |
| 1GG HTLV-II | gag 343–361 | PKDKTKVLVVQPRRPPPTQ |
| 1GH HTLV-I | gag 378–399 | PCPLCQDPTHWKRDCPRLKPT |
| 1GI HTLV-I | gag 392–411 | DCPRLKPTIPEPEPEEDALL |
| 2GI HTLV-II | gag 398–416 | DCPQLKPPQEEGEPLLLDL |
| 1EA HTLV-I | env 190–213 | LLPHSNLDHILEPSIPWKSKLLTL |
| 2EA HTLV-II | env 186–209 | LVHDSDLEHVLTPSTSWTTKILKF |
| 1EB HTLV-I | env 290–312 | HNSLILPPFSLSPVPTLGSRSRR |
| 1EC HTLV-I | env 360–378 | AIVKNHKNLLKIAQYAAQN |
| 1ED HTLV-I | env 376–392 | AQNRRGLDLLFWEQGGL |
| 1EE HTLV- | env 380–398 | RGLDLLFWEQGGLCKALQE |
| 1EF HTLV-I | env 465–488 | RQLRHLPSRVRYPHYSLILPESSL |
| 2EF HTLV-II | env 463–486 | IQALPQRLQNRHNQYSLINPETML |

The peptides were synthesized with a solid-phase technique according to the FMOC technology on an Applied Biosystems 430A machine. They were purified to 99.5% purity on a C18 column in an HPLC chromatograph, and were characterized by analytical HPLC, amino acid sequencing and amino acid analysis.

Sera

We used sera from 4 HTLV-I seropositive patients with adult T cell leukemia (a gift from dr Yorio Hinuma, Japan), one HTLV-I seropositive patient with tropical spactic paraparesis (TSP; an ethiopian immigrant to Sweden), five STLV-I antibody positive cynomolgus monkeys (found by us during testing of a large number of monkey sera, cf (5)), 15 HTLV-I seropositive intravenous drug abusers from the USA (sera typed with competitions RIPA (17, 25); a gift from dr Marjorie Robert-Guroff, National Cancer Institute, USA). We used 38 sera from Swedish blood donors as negative controls.

Immunoenzymatic antibody determination

We utilized an enzymatic antibody detection technique (Enzyme immunoassay; EIA) where the synthetic HTLV peptides dissolved at a concentration of 20 μg/ml were allowed to adsorb from a volume of 100 μl to an activated plastic surface, and thereafter allowed to react with antibodies in a patient serum, followed by enzyme(peroxidase) labelled indicator antibodies. The technique corresponds to the one we have described earlier (4, 15). As a measure of the serological reactivity (the IgG activity) directed against the respective synthetic peptide we used the difference in absorbance at 450 nm between a peptide-coated and a not-peptide-coated microplate well which had been incubated with the same serum at a dilution of 1/50.

RESULTS

TABLE 1a

In a series of 35 sera with known or probable specificity the analyses yielded the results shown below. The figures are the absorbance difference between peptide-coated and not-peptide-coated well in EIA. Only results from peptides which gave a clear and specific reactivity (absorbance difference of >= 0.3, and an absence of reactivity with the negative controls) are shown:

| 1GB | 2GB | 2GF | 1EA | 2EA | 1EB | 1EC | 1ED | 1EE | 1EF | 2EF | Our result | Known/ Probable type |
|---|---|---|---|---|---|---|---|---|---|---|---|---|
| Sera from four patients with adult T-cell leukemia. | | | | | | | | | | | | |
| 1.4 | 0.9 | 0.0 | 1.1 | 0.3 | 0.0 | 0.4 | 0.3 | 0.5 | 0.0 | 0.0 | 1 | (1) |
| 1.1 | 0.2 | 0.0 | 0.7 | 0.2 | 0.0 | 0.2 | 0.0 | 0.0 | 0.2 | 0.0 | 1 | (1) |
| 0.8 | 0.7 | 0.1 | 0.4 | 0.1 | 0.0 | 0.3 | 0.0 | 0.3 | 0.5 | 0.1 | 1 | (1) |
| 0.9 | 1.1 | 0.1 | 0.3 | 0.2 | 0.0 | 0.6 | 0.2 | 0.3 | 0.0 | 0.0 | 1 | (1) |
| Serum from one patient with tropical spastic paraparesis. | | | | | | | | | | | | |
| 0.6 | 0.1 | 0.2 | 1.5 | 0.2 | 0.5 | 0.0 | 0.0 | 0.4 | 0.0 | 0.0 | 1 | (1) |
| Sera from five STLV-I positive cynomolgus monkeys. | | | | | | | | | | | | |
| 1.7 | 1.3 | 0.6 | 0.4 | 0.1 | 0.0 | 0.0 | 0.0 | 0.3 | 0.0 | 0.0 | 1 | (1) |
| 1.6 | 0.4 | 0.0 | 0.3 | 0.1 | 0.0 | 0.2 | 0.4 | 0.0 | 0.0 | 0.0 | 1 | (1) |
| 1.6 | 0.3 | 0.1 | 1.0 | 0.3 | 0.0 | 0.0 | 0.0 | 0.0 | 0.0 | 0.0 | 1 | (1) |
| 1.5 | 0.0 | 0.0 | 1.1 | 0.3 | 0.0 | 0.0 | 0.2 | 0.4 | 0.0 | 0.0 | 1 | (1) |
| 1.5 | 0.5 | 0.0 | 0.3 | 0.1 | 0.0 | 0.6 | 0.0 | 0.0 | 0.0 | 0.0 | 1 | (1) |

TABLE 1b

Sera from 25 intravenous drug abusers, and 6 negative control sera, all from the USA (25). These sera were analyzed blindly. The results from one serum constitute one row.

| 1GB | 2GB | 2GF | 1EA | 2EA | 1EB | 1EC | 1ED | 1EE | 1EF | 2EF | Our result | Known/ Probable type |
|---|---|---|---|---|---|---|---|---|---|---|---|---|
| 0 | 0 | 0.1 | 0.2 | 0 | 0 | 0.1 | 0.2 | 0.1 | 0.2 | 0.1 | 1 | 1 |
| 0.8 | 0.8 | 0 | 1.0 | 0.5 | 1.1 | 0.4 | 1.0 | 1.4 | 0.3 | 0 | 1 | 1 |
| 0 | 0 | 0.1 | 0.1 | 0.6 | 0.1 | 0 | 0.2 | 0.4 | 0.1 | 0.4 | 2 | 2 |

TABLE 1b-continued

Sera from 25 intravenous drug abusers, and 6 negative control sera, all from the USA (25). These sera were analyzed blindly. The results from one serum constitute one row.

| 1GB | 2GB | 2GF | 1EA | 2EA | 1EB | 1EC | 1ED | 1EE | 1EF | 2EF | Our result | Known/ Probable type |
|---|---|---|---|---|---|---|---|---|---|---|---|---|
| 0 | 0 | 0 | .1 | 0 | 0 | 0 | 0 | 0 | 0 | 0 | 0 | 0 |
| 0.8 | 0 | 0 | 1.1 | 0 | 0 | 0 | 0 | 0 | 0.1 | 0 | 1 | 1 |
| 0.8 | 0.9 | 0.8 | 1.0 | 0.4 | 0.8 | 0 | 0.8 | 1.3 | 0 | 0 | 1 | 1 |
| 0.7 | 0.1 | 0 | 0.4 | 0 | 0 | 0 | 0 | 0 | 0.1 | 0 | 1 | 1 |
| 0.3 | 0.3 | 0 | 0.1 | 0.4 | 0 | 0 | 0 | 0 | 0.1 | 0.4 | 2 | 2 |
| 0 | 0.5 | 0 | 0 | 0.6 | 0.3 | 0 | 0 | 0 | 0.1 | 0.5 | 2 | 2 |
| 0 | 0 | 0 | 0 | 0 | 0 | 0 | 0 | 0 | 0 | 0 | 0 | 1 |
| 0 | 0.2 | 0 | 0 | 0.4 | 0.2 | 0 | 0.5 | 1.0 | 0.1 | 0.6 | 2 | 2 |
| 0 | 0 | 0 | 0 | 0.6 | 0.3 | 0 | 0 | 0.3 | 0.1 | 0.5 | 2 | 2 |
| 0.8 | 0.3 | 0 | 0.3 | 0 | 0 | 0 | 0.3 | 0 | 0 | 0 | 1 | 1 |
| 0 | 0 | 0 | 0 | 0 | 0 | 0 | 0 | 0 | 0 | 0 | 0 | 0 |
| 0 | 0.1 | 0 | 0 | 0 | 0 | 0 | 0 | 0 | 0 | 0 | 0 | 0 |
| 0.2 | 0.4 | 0 | 0 | 0.4 | 0.2 | 0 | 0 | 0.5 | 0 | 0.3 | 2 | 2 |
| 0 | 0 | 0 | 0.1 | 0.2 | 0 | 0 | 0 | 0 | 0 | 0 | ? | 1 |
| 0.9 | 0.4 | 0 | 0 | 0 | 0 | 0 | 0 | 0 | 0.2 | 0.1 | 1 | 1 |
| 0 | 0.2 | 0 | 0 | 0.1 | 0 | 0 | 0.5 | 0.6 | 0.1 | 0.3 | 2 | 2 |
| 0 | 0 | 0 | 0 | 0.5 | 0 | 0 | 0 | 0.2 | 0 | 0.1 | 2 | 2 |
| 0 | 0.2 | 0 | 0 | 0.6 | 0 | 0 | 0 | 0.1 | 0 | 0.1 | 2 | 2 |
| 0.1 | 0 | 0 | 0.3 | 0.1 | 0.3 | 0 | 0 | 1.0 | 0.9 | 0.1 | 1 | 1 |
| 0 | 0 | 0 | 0.4 | 0 | 0 | 0 | 0 | 0.5 | 0.2 | 0 | 1 | 1 |
| 0 | 0 | 0 | 0.5 | 0 | 0 | 0 | 0 | 0.1 | 0.1 | 0 | 1 | 1 |
| 0 | 0.2 | 0.1 | 0.2 | 0.2 | 0 | 0 | 0.2 | 0 | 0 | 0 | ? | 0 |
| 0 | 0.4 | 0 | 0 | 0 | 0 | 0 | 0 | 0 | 0 | 0 | ? | 1 |
| 0 | 0 | 0 | 0 | 0 | 0 | 0 | 0 | 0 | 0 | 0 | 0 | 0 |
| 0.3 | 0.6 | 0 | 0.3 | 0 | 0.1 | 0 | 0 | 0.2 | 0 | 0 | ? | 1 |
| 0.1 | 0.5 | 0 | 0 | 0.1 | 0 | 0 | 0 | 0 | 0 | 0.1 | 2 | 2 |
| 0.4 | 0 | 0 | 0.3 | 0 | 0 | 0 | 0 | 0 | 0 | 0 | 1 | 1 |
| 0 | 0 | 0 | 0 | 0 | 0 | 0 | 0 | 0 | 0 | 0 | 0 | 0 |

Frequency of reactivity (absorbance-difference>0.3) with 38 Swedish blood donor sera.

| 1/38 | 0/38 | 0/38 | 0/38 | 0/38 | 0/38 |
|---|---|---|---|---|---|
|  | 0/38 | 0/38 | 0/38 | 0/38 | 0/38 |

Explanation: 0: control serum, 1: HTLV-I positive serum, 2: HTIV-II positive serum, ? serum with an uncertain reactivity.

Improved Type Discrimination with a Combination of the Results from an HTLV-I and an HTLV-II Peptide.

As can be seen in table 1, EIA with a single peptide could not clearly differentiate between HTLV-I and HTLV-II. We then tried to analyze data in a two-dimensional diagram. At least two peptide pairs proved to give a relatively good type-specific discrimination (FIGS. 1 and 2). However, even with these pairs there were a few discrepancies.

Automatic Interpretation of HTLV Serotype:

To further improve the discrimination between the two HTLV-types we tried to take all results into account by multiplying the absorbances with weights according to the relative ability to discriminate for each peptide parameter. The weighted absrobances were then used for calculation of "HTLV-I-" and "HTLV-II-" points, respectively. The operations were performed in accordance with a computer program written in dBASE II as follows.

```
*HTLVPARS.CMD, A ROUTINE FOR SEROLOGICAL TYPING SERA
*INTO HTLV-I AND -II POSITIVITY.
SET INTENSITY OFF
SET TALK OFF
CLEAR
STORE "OK" TO MINDT
SET ALTERNATE TO HTLVTYP.TXT
DO WHILE MINDT="OK"
ERASE
É 1, 0 SAY "---------------------------------------------"
É 1,50 SAY "-----------------------------"
É 2,24 SAY "PROGRAM FOR HTLV-TYPING OF SERA"
É 3, 0 SAY "---------------------------------------------"
É 3,50 SAY "-----------------------------"
READ
STORE "        " TO MDBAS
```

-continued

```
É 5,5 SAY "Which is the name of the database? (S=stop) "GET MDBAS
READ
IF MDBAS="      "
   LOOP
ENDIF
IF !(MDBAS)="S"
   QUIT
ENDIF
STORE TRIM(!(MDBAS))+".DBF" TO MFDBAS
IF .NOT. FILE("&MDBAS")
   LOOP
ENDIF
CLEAR GETS
SET PRINT OFF
USE &MDBAS
SET ALTERNATE ON
SET CONSOLE OFF
? CHR(12)
? "        Results of the HTLV-typing of the serum samples registered in "
? " "
?"                the database "+MDBAS+"."
?" "
?"Nr- Sample-----     Result---------------------------------------------"
?" "
SET CONSOLE ON
SET ALTERNATE OFF
DO WHILE .NOT. EOF
   É 7,5 SAY STR(#,3)
   É 9,5 SAY "Serum number "+AOMR+" "+YR+"
   "+STR(VAL(LABNO),5)+" being tested."
   É 11,5 SAY "                                            "+;
   "                         "
   READ
   STORE 0.0 TO HTLVPOINT
   STORE 0.0 TO HTLV1POINT
   STORE 0.0 TO HTLV2POINT
   IF G2:117>0.20
      IF (G1:111/G2:117)>=1.4
         STORE HTLV1POINT+1 TO HTLV1POINT
      ENDIF
      IF (G1:111/G2:117)<=0.6
         STORE HTLV2POINT+1 TO HTLV2POINT
      ENDIF
ENDIF
IF G1:111>0.3.AND.G2:117<0.1
   STORE HTLV1POINT+1 TO HTLV1POINT
ENDIF
IF G1:111>0.3.AND.G2:117>0.3
   STORE HTLVPOINT+0.5 TO HTLVPOINT
ENDIF
IF G2:398>0.3
   IF G1:392/G2:398<0.5
      STORE HTLV2POINT+0.5 TO HTLV2POINT
   ENDIF
ENDIF
IF E2:186>0.20
   IF E1:190/E2:186<0.6
      STORE HTLV2POINT+1 TO HTLV2POINT
   ENDIF
   IF E1:190/E2:186>=1.4
      STORE HTLV1POINT+1 TO HTLV1POINT
   ELSE
      IF E1:190/E2:186>2.5
         STORE HTLV1POINT+2 TO HTLV1POINT
      ENDIF
   ENDIF
ELSE
   IF E1:190>0.5
      STORE HTLV1POINT+1 TO HTLV1POINT
   ENDIF
ENDIF
IF E1:290>0.25
   STORE HTLVPOINT+1 TO HTLVPOINT
ENDIF
IF E1:380>0.25
   STORE HTLVPOINT+1 TO HTLVPOINT
ENDIF
IF DI:24>0.25
   IF (D1:19/D1:24)>1.9
```

-continued

```
     STORE HTLV1POINT+1 TO HTLV1POINT
   ENDIF
 ENDIF
 IF (D1:19+D1:24)>2
   STORE HTLVPOINT+1 TO HTLVPOINT
 ENDIF
 IF D1:19>5
   STORE HTLVPOINT+0.5 TO HTLVPOINT
 ENDIF
 REPLACE HT1 WITH HTLV1POINT, HT2 WITH HTLV2POINT,;
   HT WITH HTLV1POINT+HTLV2POINT+HTLVPOINT
 IF HT>1.0
   IF HT>3.5
     STORE "A clear" TO MEPITHET
   ELSE
     STORE "A" TO MEPITHET
   ENDIF
   DO CASE
     CASE HTLV1POINT>HTLV2POINT.AND.HTLV1POINT>1
       REPLACE TYPE WITH "1"
       STORE MEPITHET+" serological reactivity corresponding to HTLV-I.";
         TO MTYPECOM
     CASE HTLV1POINT>HTLV2POINT
       REPLACE TYPE WITH "1?"
       STORE MEPITHET+" serological reactivity resembling that of HTLV-I.";
         TO MTYPECOM
     CASE HTLV1POINT=HTLV2POINT
       REPLACE TYPE WITH "HT"
       STORE MEPITHET+" reactivity compatible with both HTLV-I and HTLV-II";
         TO MTYPECOM
     CASE HTLV1POINT<HTLV2POINT.AND.HTLV2POINT>1
       REPLACE TYPE WITH "2"
       STORE MEPITHET+" serological reactivity corresponding to HTLV-II.";
         TO MTYPECOM
     CASE HTLV1POINT<HTLV2POINT
       REPLACE TYPE WITH "2?"
       STORE MEPITHET+" serological reactivity resembling that of HTLV-II.";
         TO MTYPECOM
   ENDCASE
 ELSE
   REPLACE TYPE WITH "00"
   STORE "The serological reactivity was too weak for typing." TO MTYPECOM
 ENDIF
 E 11,5 SAY MTYPECOM
 READ
 SET ALTERNATE ON
 SET CONSOLE OFF
 ? STR(#, 3)+"   "+AOMR+" "+YR+"
 "+STR(VAL(LABNO),5)+"   "+MTYPECOM
 SET CONSOLE ON
 SET ALTERNATE OFF
 SKIP
ENDDO
ENDDO
RETURN
```

The result is shown in FIG. 3.

In four cases the typing result was "not typable".

Two of these sera were earlier classified as HTLV-antibody negative and two were earlier typed as weakly HTLV-I reactive. Thus, in no case the peptide-typing result was clearly different from the known or probable result. Judging from this a serotyping according to our technique would not lead to false typing results, but to a small number of results in the categories "not typable", or "HTLV of indeterminate type".

DISCUSSION OF THE RESULTS OF THE TEST SERIES

Immunogenicity of HTLV Proteins

The HTLV-I and -II genomes are 50% similar at the nucleic acid level (6, 10). The similarity is larger in gag than in env. Obvious similarities are however present also in env (10). Long type-specific sequences are present primarily in env. Within the two virus species the variation is very small. This means that peptides taken from one sequence potentially can detect antibodies in many infected persons provided that their sequence is immunogenic enough. The HTLV-antigens have both been studied with conventional serology (19, 17) and with monoclonal antibodies (8, 22, 27).

Serological Reactivity in Gag:

Palker et al (23) earlier showed that the C-terminus of HTLV-I p19 contains an important epitope, which reacts with certain monoclonal antibodies in a type-specific manner. The HTLV-I and -II peptide which we used in this work (1GB and 2GB) partially correspond to the peptide which Palker studied, but they are longer. We have in a larger serological material with our two peptides from this region found that antibodies against the C-terminus are very frequent in both HTLV-I and -II positive sera, and that the combinaton of our two peptides gives a better discrimination than each peptide in itself. Our longer peptides recreate the native conformation of p19 better and has better possibilities to maintain it while bound to a solid phase, which is customary in many serological techniques. This is a prerequisite for performing the type discrimination analysis in a practical way.

We have found several other sequences in gag from HTLV-I which react with antibodies from both HTLV-I and -II seropositive persons (primarily 2GF, to a lesser extent 1GA and 2GA, data not shown). These function as general serological HTLV markers.

Serological Reactivity in Env:

We also found that the evolutionarily conserved sequences in gp21 (corresponding to peptides 1EC, 1ED and 1EE) could be used as type-common HTLV-serological markers. We found seven sera which reacted with a very conserved sequence (1ED), which is very similar to sequences in the murine leukemia virus p15E which probably has an immunosuppressive activity. This may have diagnostic implications and implications for the understanding of the pathogenesis of the diseases which are associated with HTLV (15).

It is known that the serological difference between HTLV-I and -II remains if a neutralization test with pseudotypes between VSV and HTLV is performed (10). This confirms that in the envelope there are important type-specific determinants (cf 19, 30). We have found one such determinant, here represented by the peptides 1EA and 2EA, which were derived from the outer envelope glyco-protein. In our series 10 of 15 HTLV-I positive sera and 8 of 10 HTLV-II positive sera reacted with their homologous counterpart of the two. It has been reported that human sera can react with a shorter HTLV-I peptide, which is contained within peptide 1EA, at a similar frequency (24). We found that as with the peptide pair 1GB and 2GB the combination of the peptides 1EA and 2EA was required for an optimal type discrimination. In 21 of 25 sera with known type the combination of the two peptides gave the right type. The four remaining sera reacted too weakly to allow typing. No type-discordant reactivity was observed with this pair.

It is known from bovine leukosis virus (7) that the outer envelope glycoprotein (gp56) contains both linear and conformational epitopes. Some of them contribute to the neutralization of BLV. The antibodies which we demonstrate with the three gp56 peptides thus can also indirectly become useful for detection of neutralizing HTLV antibodies. Even the C-terminal peptide 1EB reacted relatively frequently (6 of 35 known HTLV positive sera). It was however not very type specific.

Our findings underline the type specificity of the outer glycoprotein, the most variable env-protein and of the C-terminus of p19m one of the most variable parts of gag. The STLV-I positive sera reacted mainly like the HTLV-I positive sera. The reactions with many of the env peptides were however relatively weak (cf 19, 29, 30). The high degree of similarity between these two viruses from different primate species, which then is reflected also at the peptide serological level (cf 12), indicates a common ancestry which is of more recent date than the common ancestry of HTLV-1 and HTLV-II (29).

HTLV-I and -II as Medical Problems. The Need for a Stringent Serological Technique.

HTLV-I is a virus with an almost global distribution, even if the highest frequency of infected persons is present in southern Japan, the western Pacific, Carribean, Africa and southern Italy (6, 19). It is an important factor behind the diseases adult T-cell leukemia (6, 19) and tropical spastic paraparesis (21, 25). HTLV-II so far is associated with a few cases of hairy cell leukemia (6, 16, 20).

Gradually both HTLV-I and -II have become great medical problems also in countries with a relatively low percentage of infected persons. Both can be transmitted with blood, and in the USA and Japan HTLV-I antibodies are analyzed routinely in blood donations (32). Thus a large need for confirmation of the serological screening results with as dependable methods as possible has been created. It has also become important to differentiate between HTLV-I and HTLV-II infection. The importance for the patient of differentiating between the two infections is however still uncertain. Both are associated with serious diseases. It is reasonable to assume that there are important differences in the degree and type of disease which may occur in the HTLV-I and HTLV-II positive patient.

In the USA recently a surprisingly high degree of HTLV-seropositivity was found in intravenous drug abusers (14, 26). When these sera were typed most of these reactions proved to be due to HTLV-II. HTLV-II earlier was considered very rare. It is unclear from where the virus has come. Also in great Britain (28) and Italy (11) HTLV of both types has been shown to occur in intravenous drug abusers.

Current Technique for Demonstration and Typing of HTLV Infection.

In spite of widespread use HTLV serology still is an incomplete tool for demonstration and typing of HTLV infection. A large part of the initially positive findings become negative at a comprehensive analysis. Weak and indeterminate reactivities are common. Therefore there are probably a not insignificant portion of false-negative results in the serology (3). However, a number of possibilities for confirmation of initally positive findings exist.

The techniques which now are available for typing of an HTLV infection comprise virus isolation with typing, western blot with HTLV-I and HTLV-II antigen, radioimmunoprecipitation assay (RIPA) with polyacrylamide gel electrophoresis and antigen from both viruses, neutralization assay with pseudotypes of both viruses and nucleic acid amplification, possibly followed by restriction enzyme analysis, hybridization or sequencing. In western blot with HTLV-I antigen there are often few cross-reactions with HTLV-II on p19. In RIPA type specific reactions can be studied especially well. In competition RIPA type specific reactions have been demonstrated also on p24. PCR (polymerase chain reaction, a type of nucleic acid amplification) has proven to be of great potential for discriminating between the two viruses, but has so far required lymphocytes from the patient. These techniques all require comparatively much time and competence. A simple, cheap and rapid test is needed.

Computer-Aided Interpretation of Multiparametric Serological Results.

The pattern of serological reactivity with synthetic peptides often is individual (15). Therefore the sensitivity is increased when results from several synthetic peptides are combined. In a commercial test one can sometimes mix the peptides directly in the analytical well, but this means that the qualitative contribution given by each peptide is ignored. By analyzing the reactivity of each peptide the sensitivity can be kept high without loss of specificity information. The above given computer program illustrates the principle. We have later modified the program somewhat and thereby acheived a somewhat better type discrimination. The program judges if a typing can be performed with the available information. If that is not the case this is indicated. If the number of HTLV-I and HTLV-II, respectively do not differ clearly the result is classified as "HTLV antibodies demonstrated. Typing not possible". If the number of points for a certain type is at least twice as high as the number of points for the other, that type is reported. The program can easily be modified. New peptides can easily be added when their general HTLV reactivity and ability to type discriminate become approximately known. The weighting factors may have to be modified continuously depending on the reactivity of controls and increasing experience. This pattern recognition problem can be treated in many ways, among others with a learning machine approach, the multivariate analysis method and by the use of dichotomous parsing. However, these principles are not discussed here in detail. For practical reasons we have chosen a program which primarily works according to the third principle.

The New Technique

The use of a panel of synthetic peptides gives a detailed insight into the immune response to HTLV, and complements other techniques for confirmation and typing of HTLV infection. Peptides from the envelope glycoprotein gene yielded a particularly good result. The reactivity with the envelope glycoproteins is often weak in western blot, but often strong in our peptide tests. The peptide tests thus give an opportunity to demonstrate antibody activity against both envelope (env) as well as internal (gag) components, which is an important criterion of true HTLV antibody activity.

Conclusion:

In 32 sera of 36 with known or probable HTLV type we were able to correctly decide whether a serum was HTLV-I or HTLV-II positive. The discrepant sera all gave very weak reactions.

Four Additional Peptides

In addition to the above synthesized and tested peptides, we synthesized, by a similar technique, the following four peptides:

4. Blomberg J, Nilsson I, Andersson M. Viral antibody screening system that uses a standardized single dilution immunoglobulin G enzyme immunoassay with multiple antigens. J Clin Microbiol 17:1081–1091 (1983).
5. Blomberg J, Nilsson I, Kjellén L. HTLV in Sweden: Antibodies to HTLV I antigens in experimental monkeys and their caretakers. Scand J Infect Dis 17:135–139 (1985).
6. Blomberg J. HTLV-I-prototyp i en växande grupp av leukemogena virus. Läkartidningen 86:2294–2295 (1989).
7. Bruck C, Portetelle D, Burny A, Zavada J. Topographical analysis by monoclonal antibodies of BLV-gp51 epitopes involved in viral functions. Virology 122:353–362 (1982).
8. Cogniaux J, Jacquemain P C. Production of monoclonal antibodies against HTLV-I proteins recognizing surface epitopes of live infected cells. Leukemia Research 9:1117–1126 (1985).
9. Clapham P, Nagy K, Weiss R A. Pseudotypes of human T-cell leukemia virus types 1 and 2: Neutralization by patients' sera. Proc Natl Acad Sci USA 81:3083–3086 (1984).
10. Chen I S Y, McLaughlin J, Gasson J C, Clark S C, Golde D W. Molecular characterization of genome of a novel human T-cell leukemia virus. Nature 305:502–505 (1983).
11. de Rossi A, Bortolotti F, Cadrobbi P, Chieco-Bianchi L. Trends of HTlV-I and HIV infections in drug addicts. Eur J Cancer Clin Oncol 24:279–280 (1988).
12. Dracopoli N C, Turner T R, Else J G, Jolly C J, Anthony R, Gallo R C, Saxinger W C. STLV-I antibodies in feral populations of East African vervet monkeys (*Cercopithecus aethiops*). Int J Cancer 38:523–529 (1986).

| | | | |
|---|---|---|---|
| a) | HTLV-I | gag 130–197 | PVMHPHGAPPNHRPWQMKDLQAIKQEVSQAAPGSPQFMQTIRLAVQQFDPTAKDLQDLLQYLCSSLVA |
| b) | HTLV-II | gag 137–214 | PILHPPGAPSAHRPWQMKDLQAIKQEVSSSALGSPQFMQTLRLAVQQFDPTAKDLQDLLQYLCSSLVV |
| a) | HTLV-I | gag 298–349 | LRSLAYSNANKECQKLLQARGHTNSPLGDMLRACQTWTPKDKTKVLVVQPKK |
| b) | HTLV-II | gag 305–356 | LRSLAYSNANKECQKILQARGHTNSPLGEMLRTCQAWTPKDKTKVLVVQPRR |

Preliminary results support that these peptides, which are derived from p24 of HTLV-I and -II, can detect HTLV-I and HTLV-II antibodies and that they react in a type-specific way in an immunoassay according to the present invention. The distinguishing feature of these peptides in that due to their length they simulate HTLV-specific epitopes better than shorter peptides.

LITERATURE

1. Asher D M, Goudsmit J. Pomeroy K L, Garruto R M, Bakker M, Ono S G, Elliott N, Harris K, Askins H, Eldadah Z, Goldstein A D, Gajdusek D C. Antibodies to HTLV-I in populations of the south-western pacific. J Med Virol 26:339–351 (1988).
2. Ben-Ishai Z, Haas M, Triglia D, Lee V, Nahmias J, Bar-Shany S, Jensen F. Human T-cell lymphotropic virus type I antibodies in Falashas and other ethnic groups in Israel. Nature 315:665–666 (1985).
3. Blattner W A, Nomura A, Clark J W, Ho G Y F, Nakao Y, Gallo R, Robert-Guroff M. Modes of transmission and evidence for viral latency from studies of human T-cell lymphotropic virus type I in Japanese migrant populations in Hawaii. Proc Natl Acad Sci USA 83:4895–4898 (1986).
13. Gallo R C, Kalyanaraman V S, Sarngadharan M G, Sliski A, Vonderheid E C, Maeda M, Nakao Y, Yamada K, Ito Y, Gutensohn N, Murphy S, Bunn Jr P A, Catovsky D, Greaves M F, Blayney D W, Blattner W A, Jarrett W F H, zur Hausen H, Seligmann M, Brouet J C, Haynes B F, Jegasothy B V, Jaffe E S, Cossman J, Broder S, Fisher R I, Golde D W, Robert-Guroff M. Association of the human type-C retrovirus with a subset of adult T-cell cancers. Cancer Res 43:3892–3899 (1983).
14. Jason J M, McDougal S. Cabradilla C, Kalyanaraman V S, Evatt B L. Human T-cell leukemia virus (HTLV-I) p24 antibody in New York city blood product recipients. Amer J Hematol 20:129–137 (1985).
15. Klasse P J, Pipkorn R. Blomberg J. Presence of antibodies to a putatively immunosuppressive part of human immunodeficiency virus (HIV) envelope glycoprotein gp41 is strongly associated with health among HIV-positive subjects. Proc Natl Acad Sci USA 85:5225–5229 (1988).
16. Kalyanaraman V S, Sarngadharan M G, Robert-Guroff M, Miyoshi I, Blayney D, Golde D, Gallo R C. A new subtype of human T-cell leukemia virus (HTLV-II) associated with a T-cell variant of hairy-cell leukemia. Science 218:571–573 (1982).

16. Kalyanaraman V S, Sarngadharan M G, Poiesz B, Ruscetti F W, Gallo R C. Immunological properties of a type C retrovirus isolated from cultured human T-lymphoma cells and comparison to other mammalian retroviruses. J Virol 38:906–915 (1981).
17. Lee H, Swanson P, Shorty V S, Zack J A, Rosenblatt J D, Chen I S. Hight rate of HTLV-II infection in seropositive i.v. drug abusers in New Orleans. Science 28:471–475 (1989).
18. Lee T H, Coligan J E, McLane M F, Sodroski J G, Popovic M, Wong-Staal F, Gallo R C, Haseltine W, Essex M. Serological cross-reactivity between envelope gene products of type I and type II human T-cell leukemia virus. Proc Natl Acad Sci USA 81:7579–7583 (1984).
19. Manzari V, Gradilone A, Barillari G, Zani M, Collalti E, Pandolfi F, De Rossi G, Liso V, Babbo P, Robert-Guroff M, Frati L. HTLV-I is endemic in southern Italy: Detection of the first infectious cluster in a white population. Int J Cancer 36:557–559 (1985).
20. Osame M, Matsumoto M, Usuku K, Izumo S, Ijichi N, Amitani H, Tara M, Igata A. Chronic progressive myelopathy associated with elevated antibodies to human T-lymphotropic virus type I and adult T-cell leukemialike cells. Ann Neurol 21:117–122 (1987).
21. Palker T J, Tanner M E, Scearce R M, Streilein R D, Clark M E, Haynes B F. Mapping of immunogenic regions of human T cell leukemia virus type I (HTLV-I) gp46 and gp21 envelope glycoproteins with env-encoded synthetic peptides and a monoclonal antibody to gp46. J Immunol 142:971–978 (1989).
22. Palker T J, Scearce R M, Copeland T D, Oroszlan S, Haynes B F. C-terminal region of human T-cell lymphotropic virus type I (HTLV-I) p19 core protein is immunogenic in human and contains an HTLV-I-specific epitope. J Immunol 136:2393–2397 (1986).
23. Palker T J, Scearce R M, Ho W, Copeland T D, Oroszlan S, Popovic M, Haynes B F. Monoclonal antibodies reactive with human T cell lymphotropic virus I (HTLV-I) p19 internal core protein: Cross reactivity with normal tissues and differential reactivity with HTLV-I type I and II. J Immunol 135:247–253 (1985).
24. Robert-Guroff M, Weiss S H, Giron J A, Jennings A M, Ginzburg H M, Margolis I B, Blattner W A, Gallo R C. Prevalence of antibodies to HTLV-I, -II and -III in intravenous drug abusers from an AIDS endemic region. JAMA 255:3133–3137 (1986).
25. Robert-Guroff M, Gallo R C. Establishment of an etiologic relationship between the human T-cell leukemia/lymphoma virus (HTLV) and adult T-cell leukemia. Blut 47:1–12 (1983).
26. Tanaka Y, Lee B, Inoi T, Tozawa H, Yamamoto N, Hinuma Y. Antigens related to three core proteins of HTLV-I (p24, p19 and p15) and their intracellular localizations, as defined by monoclonal antibodies, Int j Cancer 37:35–42 (1986).
27. Tedder R S, Shanson D C, Jeffries D J, Cheingsong-Popov R, Clapham P, Dalgleish A, Nagy K, Weiss R A. Low prevalence in the UK of HTLV-I and HTLV-II infection in subjects with AIDS, with extended lymphadenopathy, and at risk of AIDS. Lancet ii: 125–128 (1984).
28. Tozawa H, Andoh S, Takayama Y, Tanaka Y, Lee B, Nakamura H, Hayami M, Hinuma Y. Species-dependent anti-genicity of the 34-kDa glycoprotein found on the membrane of various primate lymphocytes transformed by human T-cell leukemia virus type I (HTLV-I) and simian T-cell leukemia virus (STLV-I). Int J Cancer 41:231–238 (1988).
29. Weiss R A, Clapham P, Nagy K, Hoshino H. Envelope properties of human T-cell leukemia viruses. Curr Top Microbiol Immunol 115:235–246 (1985).
30. White P M. Comparison of assays for antibody to HTLV-I. J Clin Pathol 41:700–702 (1988).
31. Williams A E, Fang T C, Slamon D J, Poiesz B J, Sandler G S, Darr II F, Shulman G, McGowan E I, Douglas D K, Bowman R J, Peetom F, Kleinman S H, Lenes B, Dodd R Y. Seroprevalence and epidemiological correlates of HTLV-I infection in US blood donors. Science 240:643–646 (1988).

What is claimed is:

1. A method of differentiating in a test sample antibodies arising from HTLV-I infection and antibodies arising from HTLV-II infection comprising analyzing the test sample in at least four immunoassays that each employ (i) at least one synthetic peptide from each of groups a) to d):
  a) a synthetic peptide comprising 17 to 68 amino acids and at least one antigenic structure, said peptide derived from the HTLV-I gag gene;
  b) a synthetic peptide comprising at least 17 amino acids and at least one antigenic structure, said peptide derived from the HTLV-II gag gene;
  c) a synthetic peptide comprising at least 17 amino acids and at least one antigenic structure, said peptide derived from the HTLV-I env gene;
  d) a synthetic peptide comprising at least 17 amino acids and at least one antigenic structure, said peptide derived from the HTLV-II env gene; and (ii) at least one pair of synthetic peptides derived from HTLV-I and HTLV-II gene sequences selected from each of the groups a) plus b), and c) plus d);

wherein each of said immunoassays employs a different synthetic peptide selected from groups a) to d).

2. A method according to claim 1, wherein the synthetic peptides are selected from the peptides

| | | | |
|---|---|---|---|
| a) | HTLV-I  | gag 130–197 | PVMHPHGAPPNHRPWQMKDLQAIKQEVSQAAPGSPQFMQTIRLAVQQFDPTAKDLQDLLQYLCSSLVA |
| b) | HTLV-II | gag 137–214 | PILHPPGAPSAHRPWQMKDLQAIKQEVSSSALGSPQFMQTLRLAVQQFDPTAKDLQDLLQYLCSSLVV |
| a) | HTLV-I  | gag 298–349 | LRSLAYSNANKECQKLLQARGHTNSPLGDMLRACQTWTPKDKTKVLVVQPKK |
| b) | HTLV-II | gag 305–356 | LRSLAYSNANKECQKILQARGHTNSPLGEMLRTCQAWTPKDKTKVLVVQPRR |
| a) | HTLV-I  | gag 4–20    | IFSRSASPIPRPPRGLA |
| b) | HTLV-II | gag 4–20    | IHGLSPTPIPKAPRGLS |
| a) | HTLV-I  | gag 111–130 | PDSDPQIPPPYVEPTAPQVL |
| b) | HTLV-II | gag 117–136 | PSPEAHVPPPYVEPTTTQCP |
| a) | HTLV-I  | gag 265–285 | SILQGLEEPYHAFVERLNIAL |
| a) | HTLV-I  | gag 302–320 | LAYSNANKECQKLLQARGH |
| a) | HTLV-I  | gag 323–341 | SPLGDMLRACQTWTPKDKT |
| a) | HTLV-I  | gag 337–355 | PKDKTKVLVVQPKKPPPNQ |

-continued

| | | | |
|---|---|---|---|
| b) | HTLV-II | gag 343–361 | PKDKTKVLVVQPRRPPPTQ |
| a) | HTLV-I | gag 378–399 | PCPLCQDPTHWKRDCPRLKPT |
| a) | HTLV-I | gag 392–411 | DCPRLKPTIPEPEPEEDALL |
| b) | HTLV-II | gag 398–416 | DCPQLKPPQEEGEPLLLDL |
| c) | HTLV-I | env 190–213 | LLPHSNLDHILEPSIPWKSKLLTL |
| d) | HTLV-II | env 186–209 | LVHDSDLEHVLTPSTSWTTKILKF |
| c) | HTLV-I | env 290–312 | HNSLILPPFSLSPVPTLGSRSRR |
| c) | HTLV-I | env 360–378 | AIVKNHKNLLKIAQYAAQN |
| c) | HTLV-I | env 376–392 | AQNRRGLDLLFWEQGGL |
| c) | HTLV-I | env 380–398 | RGLDLLFWEQGGLCKALQE |
| c) | HTLV-I | env 465–488 | RQLRHLPSRVRYPHYSLILPESSL |
| d) | HTLV-II | env 463–486 | IQALPQRLQNRHNQYSLINPETML. |

3. A method according to claim 2, wherein the following peptides are selected:

| | | | |
|---|---|---|---|
| a) | HTLV-I | gag 111–130 | PDSDPQIPPPYVEPTAPQVL |
| b) | HTLV-II | gag 117–136 | PSPEAHVPPPYVEPTTTQCP |
| c) | HTLV-I | env 190–213 | LLPHSNLDHILEPSIPWKSKLLTL |
| d) | HTLV-II | env 186–209 | LVHDSDLEHVLTPSTSWTTKILKF. |

4. A method according to claim 1 wherein the sample to be analyzed is subjected to at least eight immunoassays.

5. A method according to claim 1, wherein at least one of the synthetic peptides is attached to an inert soluble of insoluble carrier.

6. A peptide consisting of at least one antigenic structure for HTLV-I or HTLV-II selected from the following sequences:

| | | |
|---|---|---|
| HTLV-I | gag 298–349 | LRSLAYSNANKECQKLLQARGHTNSPLGMLRACQTWTPKDKTKVLVVQPKK |
| HTLV-II | gag 4–20 | IHGLSPTPIPKAPRGLS |
| HTLV-I | gag 111–130 | PDSDPQIPPPYVEPTAPQVL |
| HTLV-II | gag 117–136 | PSPEAHVPPPYVEPTTTQCP |
| HTLV-I | gag 265–285 | SILQGLEEPYHAFVERLNIAL |
| HTLV-I | gag 302–320 | LAYSNANKECKLLQARGH |
| HTLV-I | gag 323–341 | SPLGDMLRACQTWTPKDKT |
| HTLV-I | gag 337–355 | PKDKTKVLVVQPKKPPPNQ |
| HTLV-II | gag 343–361 | PKDKTKVLVVQPRRPPPTQ |
| HTLV-I | gag 378–399 | PCPLCQDPTHWKRDCPRLKPT |
| HTLV-I | gag 392–411 | DCPRLKPTIPEPEPEEDALL |
| HTLV-II | gag 398–416 | DCPQLKPPQEEGEPLLLDL |
| HTLV-II | env 186–209 | LVHDSDLEHVLTPSTSWTTKILKF |
| HTLV-I | env 290–312 | HNSLILPPFSLSPVPTLGSRSRR |
| HTLV-I | env 376–392 | AQNRRGLDLLFWEQGGL |
| HTLV-I | env 380–398 | RGLDLLFWEQGGLCKALQE |
| HTLV-I | env 465–488 | RQLRHLPSRVRYPHYSLILPESSL |
| HTLV-II | env 463–486 | IQALPQRLQNRHNQYSLINPETML. |

7. A method of detecting HTLV-I or HTLV-II antibodies in a test sample, comprising analyzing said test sample in an immunoassay that employs at least one peptide of claim 6.

8. An immunoassay kit for differentiating in a test sample antibodies arising from HTLV-I infection and antibodies arising from HTLV-II infection comprising one or more containers holding synthetic peptides for analyzing a test sample in at least four immunoassays, said synthetic peptides comprising at least one peptide selected from each of groups a) to d):

a) a synthetic peptide comprising at least 17 amino acids and at least one antigenic structure, said peptide derived from the HTLV-I qag gene;

b) a synthetic peptide comprising at least 17 amino acids and at least one antigenic structure, said peptide derived from the HTLV-II gag gene;

c) a synthetic peptide comprising at least 17 amino acids and at least one antigenic structure, said peptide derived from the HTLV-I env gene; and d) a synthetic peptide comprising at least 17 amino acids and at least one antigenic structure, said peptide derived from the HTLV-II env gene.

9. An immunoassay kit according to claim 8, wherein it comprises at least four peptides selected from the peptides

| | | | |
|---|---|---|---|
| a) | HTLV-I | gag 130–197 | PVMHPHGAPPNHRPWQMKDLQAIKQEVSQAAPGSPQFMQTIRLAVQQFDPTAKDLQDLLQYLCSSLVA |
| b) | HTLV-II | gag 137–214 | PILHPPGAPSAHRPWQMKDLQAIKQEVSSSALGSPQFMQTLRLAVQQFDPTAKDLQDLLQYLCSSLVV |
| a) | HTLV-I | gag 298–349 | LRSLAYSNANKECQKLLQARGHTNSPLGDMLRACQTWTPKDKTKVLVVQPKK |
| b) | HTLV-II | gag 305–356 | LRSLAYSNANKECQKILQARGHTNSPLGEMLRTCQAWTPKDKTKVLVVQPRR |
| a) | HTLV-I | gag 4–20 | IFSRSASPIPRPPRGLA |
| b) | HTLV-II | gag 4–20 | IHGLSPTPIPKAPRGLS |
| a) | HTLV-I | gag 111–130 | PDSDPQIPPPYVEPTAPQVL |

| | | | |
|---|---|---|---|
| b) | HTLV-II | gag 117–136 | PSPEAHVPPPYVEPTTTQCP |
| a) | HTLV-I | gag 265–285 | SILQGLEEPYHAFVERLNIAL |
| a) | HTLV-I | gag 302–320 | LAYSNANKECQKLLQARGH |
| a) | HTLV-I | gag 323–341 | SPLGDMLRACQTWTPKDKT |
| a) | HTLV-I | gag 337–355 | PKDKTKVLVVQPKKPPPNQ |
| b) | HTLV-II | gag 343–361 | PKDKTKVLVVQPRRPPPTQ |
| a) | HTLV-I | gag 378–399 | PCPLCQDPTHWKRDCPRLKPT |
| a) | HTLV-I | gag 392–411 | DCPRLKPTIPEPEPEEDALL |
| b) | HTLV-II | gag 398–416 | DCPQLKPPQEEGEPLLLDL |
| c) | HTLV-I | env 190–213 | LLPHSNLDHILEPSIPWKSKLLTL |
| 4) | HTLV-II | env 186–209 | LVHDSDLEHVLTPSTSWTTKILKF |
| c) | HTLV-I | env 290–312 | HNSLILPPFSLSPVPTLGSRSRR |
| c) | HTLV-I | env 360–378 | AIVKNHKNLLKIAQYAAQN |
| c) | HTLV-I | env 376–392 | AQNRRGLDLLFWEQGGL |
| c) | HTLV-I | env 380–398 | RGLDLLFWEQGGLCKALQE |
| c) | HTLV-I | env 465–488 | RQLRHLPSRVRYPHYSLILPESSL |
| d) | HTLV-II | env 463–486 | IQALPQRLQNRHNQYSLINPETML. |

10. An immunoassay kit according to claim 9, wherein it comprises at least the following peptides:

| | | | |
|---|---|---|---|
| a) | HTLV-I | gag 111–130 | PDSDPQIPPPYVEPTAPQVL |
| b) | HTLV-II | gag 117–136 | PSPEAHVPPPYVEPTTTQCP |

-continued

| | | | |
|---|---|---|---|
| c) | HTLV-I | env 190–213 | LLPHSNLDHILEPSIPWKSKLLTL |
| d) | HTLV-II | env 186–209 | LVHDSDLEHVLTPSTSWTTKILKF. |

\* \* \* \* \*

UNITED STATES PATENT AND TRADEMARK OFFICE
CERTIFICATE OF CORRECTION

| | |
|---|---|
| PATENT NO. : 6,242,174 B1 | Page 1 of 1 |
| DATED : June 5, 2001 | |
| INVENTOR(S) : Jonas Blomberg and Rudiger Pipkorn | |

It is certified that error appears in the above-identified patent and that said Letters Patent is hereby corrected as shown below:

Title page,
Line 22, "Filed: Oct. 7, 1991" should be deleted and the following should be added:
-- PCT Filed: Mar. 2, 1990
Item [86], PCT No.: PCT/SE90/00139
  § 371 Date: October 7, 1991
  § 102(e) Date: October 7, 1991
Item [87] PCT Pub. No.: WO 90/10231
  PCT Pub. Date: Sep. 7, 1990 --

Item [30] Foreign Application Priority Data, the following should be deleted:
"Mar. 2, 1990 (WO)    PCT/SE90/00139"

Signed and Sealed this

Fifth Day of March, 2002

*Attest:*

*Attesting Officer*

JAMES E. ROGAN
*Director of the United States Patent and Trademark Office*